US005088925A

United States Patent [19]

Mason

[11] Patent Number: 5,088,925

[45] Date of Patent: Feb. 18, 1992

[54] INSTRUMENT AND METHOD FOR ADMINISTERING AN INJECTABLE ANESTHETIC

[76] Inventor: William E. Mason, 100 Harrow La., Saginaw, Mich. 48603

[21] Appl. No.: 622,970

[22] Filed: Dec. 6, 1990

[51] Int. Cl.[5] .......... A61C 3/00; A61M 5/00

[52] U.S. Cl. .......... 433/141; 604/112

[58] Field of Search .......... 433/141; 604/112, 115, 604/116; 606/201, 204

[56] References Cited

U.S. PATENT DOCUMENTS

| | | | |
|---|---|---|---|
| 722,019 | 3/1903 | Hildebrandt et al. | 604/315 |
| 1,138,881 | 5/1915 | McFarland | 604/315 |
| 1,148,093 | 7/1915 | Kells | 604/313 |
| 1,561,116 | 11/1925 | Silliman | 604/115 |
| 1,934,046 | 11/1933 | Demarchi | 604/115 |
| 2,479,645 | 4/1948 | Silverstein | 433/141 |
| 2,597,966 | 5/1952 | Adler | 128/67 |
| 2,945,496 | 7/1960 | Fosdal | 604/115 |
| 3,399,675 | 10/1968 | Hill | 604/112 |
| 3,620,209 | 11/1971 | Kravitz | 604/112 |
| 4,759,713 | 7/1988 | Heiss et al. | 433/141 |
| 4,795,344 | 1/1989 | Brewer, Jr. | 433/141 |
| 4,836,781 | 6/1989 | Meinershagen | 433/141 |

OTHER PUBLICATIONS

Handbook of Local Anesthesia by Stanley F. Malamed, D.D.S. Copyright 1980 by The C. V. Mosby Company, pp. 145-161 and pp. 181-186.

*Primary Examiner*—John J. Wilson
*Assistant Examiner*—Cindy Cherichetti
*Attorney, Agent, or Firm*—Learman & McCulloch

[57] ABSTRACT

A method of administering an injectable anesthetic to the palatal tissue covering one of the foramina of the palate with a hypodermic syringe and a specialized instrument. The instrument has a handle with stem ends, the right hand end and left hand stem end each having a compositely angled shank part connected to a ring to be disposed flatwise on the palatal tissue. The ring at each end presents a blunted bottom to the palatal tissue. The ring further has a through slit therein. Firstly the instrument is placed in the patient's mouth with one of the rings in contact with the palatal tissue immediately adjacent to one of the foramina. The ring is firmly pressed against the palatal tissue until the tissue blanches and a pressure anesthesia through ischemia is achieved. Then a hypodermic syringe is placed in the mouth of the patient, and the needle is inserted through and guided by the ring into the very center of the palatal tissue. After that, the instrument is removed by passing the slit in the ring past the inserted needle, and then a liquid anesthetising drug is injected into the palatal tissue.

20 Claims, 1 Drawing Sheet

INSTRUMENT AND METHOD FOR ADMINISTERING AN INJECTABLE ANESTHETIC

BACKGROUND OF THE INVENTION

The present invention is concerned with the field of anesthetic injection of the palatal tissue and more particularly to a method and instrument which can be readily used by dentists, for example, to deaden or eliminate the pain associated with the penetration of the needle into the relatively thin and sensitive palatal tissue. Various instruments have been proposed over the years to aid in the injection of anesthetics or the withdrawal of blood, as set forth in the following prior art patents:

| | |
|---|---|
| 1,561,116 | Silliman |
| 2,945,496 | Fosdal |
| 4,795,344 | Brewer, Jr. |
| 4,836,781 | Meinershagen |

None of the foregoing patents are, however, particularly concerned with injection at the palatal foramina where the nerves are exposed in the bone and the soft tissue is fibrous and taut. In the Fosdal U.S. Pat. No. 2,945,496, a dental instrument is suggested for gum tissue. In this instrument, a foot having top and bottom openings is placed on the gum tissue with only enough pressure to seal the opening for the application of suction. The upper opening in the foot is covered with a jacket of transparent material and, when the gum tissue is sucked up into the foot through the bottom opening, a hypodermic needle is inserted through the jacket and into the gum tissue to progressively feed a pain killing drug into the tissue. The Fosdal patent postulates that suction drawing the tissue into the interior of the foot causes the tissue to become taut, firm and immobile and that this preconditioning minimizes the shock of needle penetration. In effect, the instrument used applies a negative pressure which, as will become apparent, is the antithesis of what the present method teaches. The instrument requires movable tissue such as to be found in the gums but not in the thin, taut palatal tissue. The other patents cited are also considered not materially pertinent to the invention claimed, which is neither singularly nor combinatively disclosed or suggested in these prior art patents.

Another method which has been recommended is the use of a swab stick at a site adjacent the area to be injected, while the needle is inserted adjacent to the tissue which is pressed until it blanches by the swab stick. The swab stick may undesirably leave cotton fibers in the tissue and, more importantly, presses only a very small spot at one side of the tissue which is to be injected.

SUMMARY OF THE INVENTION

The method of pain alleviation utilized in the thin, and therefore very sensitive palatal tissue covering the palative bone employs a positive pressure to stimulate the surface tactile receptors of the palatal tissue to be injected to thereby "open the gate" of the pain transmitting fibers and interrupt their transmission to the brain. At the same time, a pressure anesthesia through ischemia is effected at the selected location. In using the instrument which will be described, the dentist firmly presses one of the ring ends of the instrument against the palatal tissue immediately adjacent to the foramen selected, until the tissue visibly blanches. The syringe needle is then gently inserted into the tissue through the open center of the instrument's ring, which also functions to provide a bullseye target, to a site just below the tissue surface, after which the instrument is slowly removed by drawing the exit slit in the instrument end past the needle. Thereafter a small amount of anesthetic is slowly administered until the tissue blanches slightly, after which the syringe is removed. After the initial anesthetic takes effect a few minutes later, further anesthetic may be administered without discomfort to the patient. The tissue immediately adjacent to that covering each of the remaining palatal foramina may be subsequently anesthetized in the same way. The instrument utilized in the method is a double ended instrument with one end being used for the right anterior palatine foramen and the other for the left anterior palatine foramen. Either end may be used for the naso-palatine foramen. The instrument includes a gripping base with compositely angled shanks at each end which terminate in a ring. The slit provided in each of the ring ends permits the instrument to be withdrawn past the needle, once the needle is inserted centrally through the ring into the palatal tissue.

One of the prime objects of the present invention is to provide a specialized instrument for the performance of the new method of injecting the palatal tissue in a manner which relieves the pain and resulting mental trauma associated with the administration of an anesthetic to this tissue by the needle.

Still another object of the invention is to provide an instrument which can be easily and efficiently used to inject the palatal tissue immediately adjacent that covering the exposed nerves at all of the palatal foramina, one after the other.

Still a further object of the invention is to provide an instrument which is light in weight, yet sturdy, and which further is of simple and inexpensive construction.

Other objects and advantages of the invention will be pointed out specifically or will become apparent from the following description when it is considered in conjunction with the appended claims and the accompanying drawings.

Figure 1:
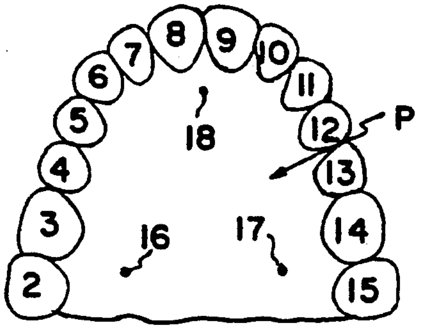
FIG. 1 is a schematic under plan view of the palate showing the location of the palatal foramina relative to the teeth and gum tissue.

Referring now more particularly to the accompanying drawings wherein a preferred embodiment of the invention is disclosed, and in the first instance more particularly to FIG. 1, the upper teeth are numbered in the usual fashion and the palatal tissue is generally identified by the letter P. The right anterior palatine foramen is identified at 16 and the left anterior palatine foramen is identified at 17. The naso-palatine foramen is identified at 18.

Figure 2:
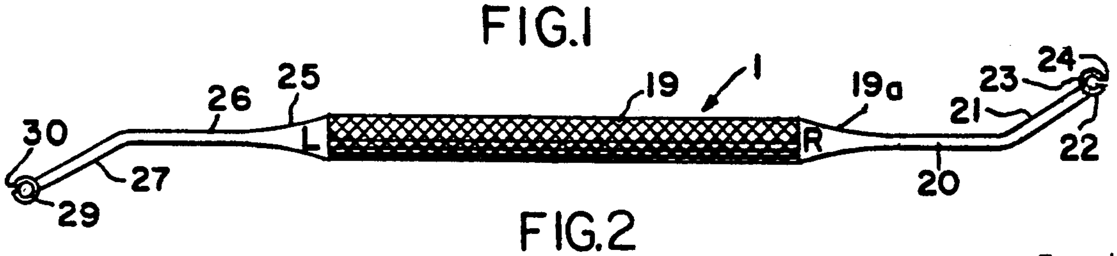
FIG. 2 is a top plan view of the specialized instrument utilized in the process.
Figure 3:
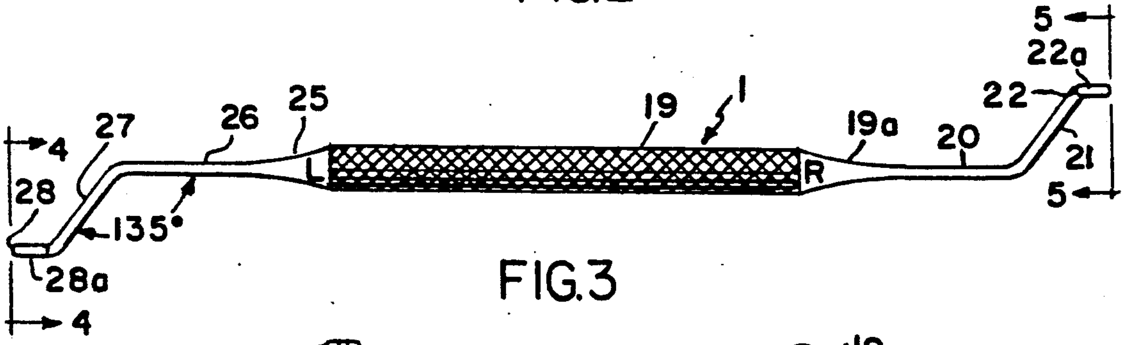
FIG. 3 is a side elevational view thereof.
Figure 5:
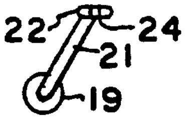
FIG. 5 is an end elevational view taken on the line 5—5 of FIG. 2, with the opposite end of the instrument omitted from the view.
Figure 4:
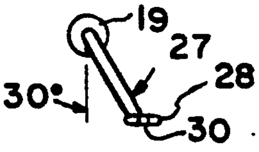
FIG. 4 is an end elevational view taken on the line 4—4 of FIG. 2, and with the opposite end of the instrument omitted from the view.

The instrument I to now be described is of a specialized structure to aid in the administration of the anesthetic which is conventionally injected at these locations during the practice of various dental procedures requiring anesthesia of the palatal tissue. The instrument I comprises a knurled mid or base portion 18 which at its right end includes a transition portion 19 leading to the stem portion 20 of reduced diameter. A shank 21 extends angularly from the part 20 in a compound manner and terminates in a ring 22 which is flat in the sense that it is parallel with the stem portion 20 and base portion 18 in FIG. 3. Ring 22 is circular in cross-section to present a blunted, or curvilinear surface 22a to the palatal tissue. The ring opening 23 of predetermined diameter communicates with a through slit 24 of predetermined width in the terminal end of ring 22. As will be apparent from FIG. 2, the portion 19 of the instrument bears the indicia R so that the person using the instrument can readily distinguish the right and left hand ends.

At the other end of the instrument I, the intermediate base portion 18 has a similar transition portion 25 leading to a reduced diameter stem portion 26. A shank 27 then extends angularly from the portion 26 and terminates in a left end ring 28 which is parallel to the stem portion 26 and base 18 in FIG. 3. Ring 28 similarly is of circular cross-section to present a blunted outer curvilinear surface 28a to the palatal tissue and the opening 29. The ring 28 similarly has an opening 29 of predetermined diameter, and has a through slit 30 of predetermined width communicating with it.

The rings 22 and 28 are four millimeters in external diameter, and openings 23 and 29 are two millimeters in diameter. The slits 24 and 30 are one millimeter in width to provide the desired escape past the hypodermic needle. The cross-sectional diameter of the ring 23 is also one millimeter, and the length of shanks 21 and 27 is fourteen millimeters. The angle of the shanks 21 and 27 to the stem portions 20 and 26 is 135° and the offset angle of the shanks 28 and 27 to the portions 20 and is 30°. These angles have been found to best present the rings 24 and 28 to the palatal tissue while still providing the vision which the dentist needs to properly place the instrument ends and insert the needle through the center of the ring end in use.

In practice, the instrument is held in the left hand by a right handed operator with the right end being used at the right anterior palatin foramen and the left end being used at the left anterior palatal foramen. While either end may be used for the naso-palatine foramen, for a right handed operator, the left end is more convenient.

Figure 6:
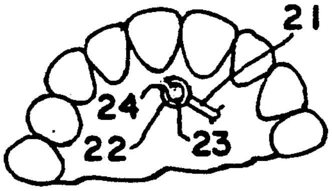
FIGS. 6–8 are progressive fragmentary underplan views illustrating the steps which are progressively performed in practicing the method.
Figure 7:
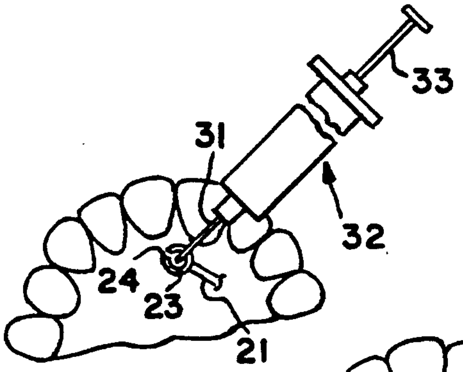
Figure 8:
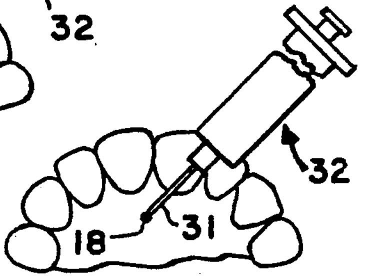

In practicing the method, it will be noted that in FIGS. 6–8 it is the naso-palatine foramen tissue to which the pain killing anesthetic is being administered. Prior to the time the ring 22 is applied to the tissue immediately adjacent to the foramen 18, as disclosed in FIG. 6, the dentist drys the foramen area and applies a topical anesthetic. After a time wait of approximately one minute for the surface tissue to be anesthetized, the ring 22 is pressed firmly into the palatal tissue immediately adjacent to the foramen 18 until the tissue visibly blanches. The ring end is applied at the base of the incisive papilla, just lateral of it. At this point the syringe needle 31 of the drug-containing hypodermic syringe 32 is inserted into the mouth of the patient, with the syringe needle 32 gently inserted through the open center of the opening 23 as a bullseye target to a level just below the thin tissue surface, i.e. 6–10 millimeters. The needle, which preferably is approaching the injection site at a forty-five degree angle, engages and is guided by the ring into substantially the very center of the blanched tissue for maximum patient comfort. Preferably the drug or anesthetic will be warmed just prior to injection to prevent a "burning" sensation when the anesthetic is being administered. After insertion of the needle, the instrument I is then slowly withdrawn, with slit 24 being moved past the needle 31. This is a safety measure so the dentist has a free hand at the time of anesthetic injection in case the patient gags or needs to swallow. Then the syringe plunger 33 is pressed and a small amount of anesthetic is very slowly administered until the tissue blanches slightly. Following this, the needle 31 is removed. A few minutes later, further anesthetic may be administered after the initial amount has fully deadened the tissue. The method is effective, simple to implement, and of great benefit to the patient. The anterior foramina 16 and 17 are treated in the same way with the ring end being pressed against the tissue immediately anterior to the foramen 16 or foramen 17. Because there is no papilla, the site is selected as the area midway between the rearmost and next rearmost molars, and halfway in the palatal tissue between the gum line and the longitudinal midpoint of the palatal tissue. The normal depth of insertion used is 10–15 millimeters.

Although preferred embodiments of the invention have been illustrated in the accompanying drawings and described in the foregoing detailed description, it will be understood that the invention is not limited to the embodiments disclosed, but is capable of numerous rearrangements, modifications and substitutions of parts and elements without departing from the spirit of the invention which is defined in the following claims.

What is claimed is:

1. In a method of administering an injectable anesthetic to the palatal tissue adjacent one of the foramina of the palate with a hypodermic syringe and an instrument comprising a handle with at least one instrument end having an angularly turned part connected to a ring, the ring having an inner opening and a surrounding surface with a blunted bottom which contacts the portion of the palatal tissue substantially immediately adjacent one of the foramina, the ring further having a through slit therein, the steps of:

a. placing the instrument in the patient's mouth with the said surrounding surface of the ring in contact with the palatal tissue immediately adjacent to one of the foramina and firmly pressing the ring against the said palatal tissue until the tissue blanches and a pressure anesthesia through ischemia is achieved, b. entering the mouth of the patient with a hypodermic syringe containing an anesthetic which is injectable via the hypodermic needle of the syringe, and inserting the needle through said ring into the tissue surrounded by the ring;

c. removing the instrument from the palatal tissue by passing the slit in the ring past the inserted needle and injecting anesthetic into the parallel tissue; and d. said instrument being a double ended instrument and the handle having an opposite end except that it is a left hand version with the angularly turned part turned in the opposite direction, and said method being practiced on one of the right and left anterior foramen and then being practiced with the opposite end of the instrument on the other of the right and left anterior foramen.

2. The method of claim 1 wherein the palatal tissue to be injected is dried and covered with a topical anesthetic prior to step a.

3. The method of claim 1 wherein initially only a small amount of anesthetic is injected until the tissue blanches slightly and, after a delay for the anesthetic to take effect, further anesthetic is injected.

4. The method of claim 3 wherein said syringe and needle are removed during said delay.

5. The method of claim 1 wherein said ring is of generally circular cross-section to present a curvilinear surface to the palatal tissue.

6. The method of claim 1 wherein said ring is substantially circular and has an opening two millimeters in diameter.

7. The method of claim 6 wherein said slit is in the terminal end of the ring and is one millimeter in width.

8. A specialized instrument for assisting in administering an injectable anesthetic to the palatal tissue immediately adjacent one of the foramina of the palate in cooperation with a hypodermic syringe containing an anesthetic drug comprising:

a. a handle with an instrument end having an angularly turned part connected to a ring extending flatwise relative to the angularly turned part;
b. the ring having an inner target opening and being configured to present a blunted bottom to the palatal tissue substantially immediately adjacent to one of the foramina;
c. the ring further having a through slit therein for passing it past a hypodermic needle; and
d. said handle having a second angularly turned part on its opposite end connected to a ring extending flatwise to the angularly turned part, the second angularly turned part being extended at an angle 180° removed from said first mentioned angularly turned part.

9. The instrument of claim 8 wherein said each ring is of generally circular cross-section to present a curvilinear surface to the palatal tissue.

10. The instrument of claim 9 wherein each said ring is substantially circular and substantially four millimeters in external diameter, and each has an opening substantially two millimeters in diameter.

11. The instrument of claim 9 wherein the angularity of the angularly turned part is substantially 135° relative to the handle in side elevation and substantially 30° relative to the handle in place.

12. The instrument of claim 11 wherein the rings are substantially four millimeters in external diameter, have openings of substantially two millimeters in diameter, and have slits of substantially one millimeter in width.

13. The instrument of claim 8 wherein the angularity of the angularly turned parts is compound, the parts being turned to provide an obtuse angle with the handle in plan and an acute angle with the handle in side elevation.

14. In a method of administering an injectable anesthetic to the palatal tissue covering one of the foramina of the palate with a hypodermic syringe and an instrument comprising a handle with at least one instrument end having an angularly turned part connected to a ring, the ring having an inner opening and a surrounding surface with a blunted bottom which contacts the portion of the parallel tissue substantially immediately adjacent one of the foramina, the steps of:

a. placing the instrument in the patient's mouth with the said surrounding surface of the ring in contact with the palatal tissue immediately adjacent one of the foramina and firmly pressing the ring against the said palatal tissue until the tissue blanches and a pressure anesthesia through ischemia is achieved,
b. entering the mouth of the patient with a hypodermic syringe containing an anesthetic which is injectable via the hypodermic needle of the syringe, and, utilizing the ring as a bullseye, inserting the needle through approximately the center of said ring into the center portion of the blanched tissue;
c. injecting anesthetic into the palatal tissue covering said one of the foramina; and
d. said instrument being a double ended instrument and the handle having an opposite instrument end except that it is an opposite hand version with the angularly turned part turned in the opposite direction, said method being practiced on one of the right and left anterior foramen and then being practiced with the opposite end of the instrument on the other of the right and left anterior foramen.

15. The method of claim 14 wherein said ring is substantially circular and has an opening two millimeters in diameter.

16. A specialized instrument for assisting in administering an injectable anesthetic to the palatal tissue covering one of the foramina of the palate in cooperation with a hypodermic syringe containing an anesthetic drug comprising:

a. a handle with an instrument end having an angularly turned part connected to a ring extending flatwise relative to the angularly turned part;
b. the ring having an inner target opening and being configured to present a blunted bottom to the palatal tissue substantially immediately surrounding one of the foramina;
c. the ring further having a through slit therein;
d. said instrument being a double ended instrument and the handle having an opposite instrument end except that it is an opposite hand version with the angularly turned part turned in the opposite direction to permit the method to be practiced first on one of the right and left anterior foramen and then on the other of the right and left anterior foramen.

17. The instrument of claim 16 wherein each ring is of generally circular cross-section.

18. A specialized instrument for assisting in administering an injectable anesthetic to the palatal tissue covering one of the foramina of the palate in cooperation with a hypodermic syringe containing an anesthetic drug comprising:

a. a handle with an instrument end having an angularly turned part connected to a ring extending flatwise relative to the angularly turned part;
b. the ring having an inner target opening and being configured to present a blunted bottom to the palatal tissue substantially immediately surrounding one of the foramina;
c. the angularity of the angularly turned part being compound, the part being turned to provide an obtuse angle with the handle in plan and an acute angle with the handle in side elevation.

19. The instrument of claim 18 wherein said ring is of generally circular cross-section, and is substantially circular, the ring being substantially four millimeters in external diameter, and having an opening substantially two millimeters in diameter.

20. The instrument of claim 18 wherein the angularity of the angularly turned part is substantially 135° relative to the handle in side elevation and substantially 30° relative to the handle in plan.

* * * * *

UNITED STATES PATENT AND TRADEMARK OFFICE
CERTIFICATE OF CORRECTION

PATENT NO. : 5,088,925

DATED : February 18, 1992

INVENTOR(S) : William E. Mason

It is certified that error appears in the above-identified patent and that said Letters Patent is hereby corrected as shown below:

Column 3, line 42, after "and"(second occurence), insert -- 26 --.

Signed and Sealed this

First Day of June, 1993

Attest:

Michael K. Kirk

MICHAEL K. KIRK

*Attesting Officer* *Acting Commissioner of Patents and Trademarks*